US00PP25615P2

(12) United States Plant Patent
Oudshoom

(10) Patent No.: US PP25,615 P2
(45) Date of Patent: Jun. 2, 2015

(54) ***MONARDA* PLANT NAMED 'PURPLE LACE'**

(50) Latin Name: *Monarda didyma*
Varietal Denomination: Purple Lace

(71) Applicant: Hubertus Gerardus Oudshoom, Rijpwetering (NL)

(72) Inventor: Hubertus Gerardus Oudshoom, Rijpwetering (NL)

(73) Assignee: Future Plants V.O.F., Lisserbrock (NL)

( * ) Notice: Subject to any disclaimer, the term of this patent is extended or adjusted under 35 U.S.C. 154(b) by 85 days.

(21) Appl. No.: 13/998,031

(22) Filed: Sep. 24, 2013

(51) Int. Cl.
*A01H 5/02* (2006.01)

(52) U.S. Cl.
USPC ..... Plt./455

(58) Field of Classification Search
USPC ..... Plt./455
CPC ..... A01H 5/02; A01H 5/00
See application file for complete search history.

*Primary Examiner* — Kent L Bell
(74) *Attorney, Agent, or Firm* — Penny J. Aguirre

(57) ABSTRACT

A new cultivar of *Monarda*, 'Purple Lace', that is characterized by its inflorescences that are deep red purple in color, its strong stem that are yellow-green in color, its compact plant habit, its good basal branching, and its height of about 36 cm.

2 Drawing Sheets

Botanical classification: *Monarda didyma.*
Variety denomination: 'Purple Lace'.

BACKGROUND OF THE INVENTION

The present invention relates to a new and distinct cultivar of *Monarda didyma*. The new cultivar will be referred to hereafter by its cultivar name, 'Purple Lace'. 'Purple Lace' represents a new cultivar of bee balm suitable for use as a garden plant.

The new cultivar arose from on ongoing breeding program conducted by the Inventor in Lisserbroek, The Netherlands. 'Purple Lace' arose from a cross made in 2010 between 'Cranberry Lace' (U.S. Plant patent application Ser. No. 13/385,839, abandoned) as the female parent and 'Pink Lace' (U.S. Plant Pat. No. 18,367) as the male parent. The new cultivar was selected in July of 2011 as a single unique plant from the above cross.

Asexual propagation of the new cultivar was first accomplished by stem cuttings by the Inventor in 2012 in Lisserbroek, The Netherlands. Asexual propagation by cuttings and tissue culture has determined that the characteristics of the new cultivar are stable and are reproduced true to type in successive generations.

SUMMARY OF THE INVENTION

The following traits have been repeatedly observed and represent the characteristics of the new *Monarda*. These attributes in combination distinguish 'Purple Lace' as a unique cultivar of *Monarda.*

1. 'Purple Lace' exhibits inflorescences that are deep red purple in color.
2. 'Purple Lace' exhibits strong stem that are yellow-green in color.
3. 'Purple Lace' exhibits a compact plant habit with good basal branching.
4. 'Purple Lace' reaches a height of about 36 cm.

The new cultivar of *Monarda* can be readily distinguished from other cultivars. The parent plants of 'Purple Lace', 'Cranberry Lace' and 'Pink Lace' are the closest comparison cultivars known to the Inventor. 'Cranberry Lace' differs from 'Purple Lace' in being slightly taller in height and in having inflorescences that are bright pink in color. 'Pink Lace' differs from 'Purple Lace' in being slightly taller in height and in having inflorescences that are lighter red-purple in color. 'Purple Lace' can also be compared to the cultivars 'Fireball' (U.S. Plant Pat. No. 14,235) and 'Pink Supreme' (U.S. Plant Pat. No. 14,204). Both differ from 'Purple Lace' in being much taller in height. In addition, 'Fireball' differs in having flowers that are redder in color and 'Pink Supreme' differs in having flowers that are pink in color.

BRIEF DESCRIPTION OF THE DRAWINGS

The accompanying colored photographs illustrate the overall appearance and distinct characteristics of two year-old plants of the new *Monarda* as grown outdoors in a 17-cm container in Rijpwetering, The Netherlands.

The Photograph in FIG. 1 provides a side view of 'Purple Lace' in bloom.

Figure 1:
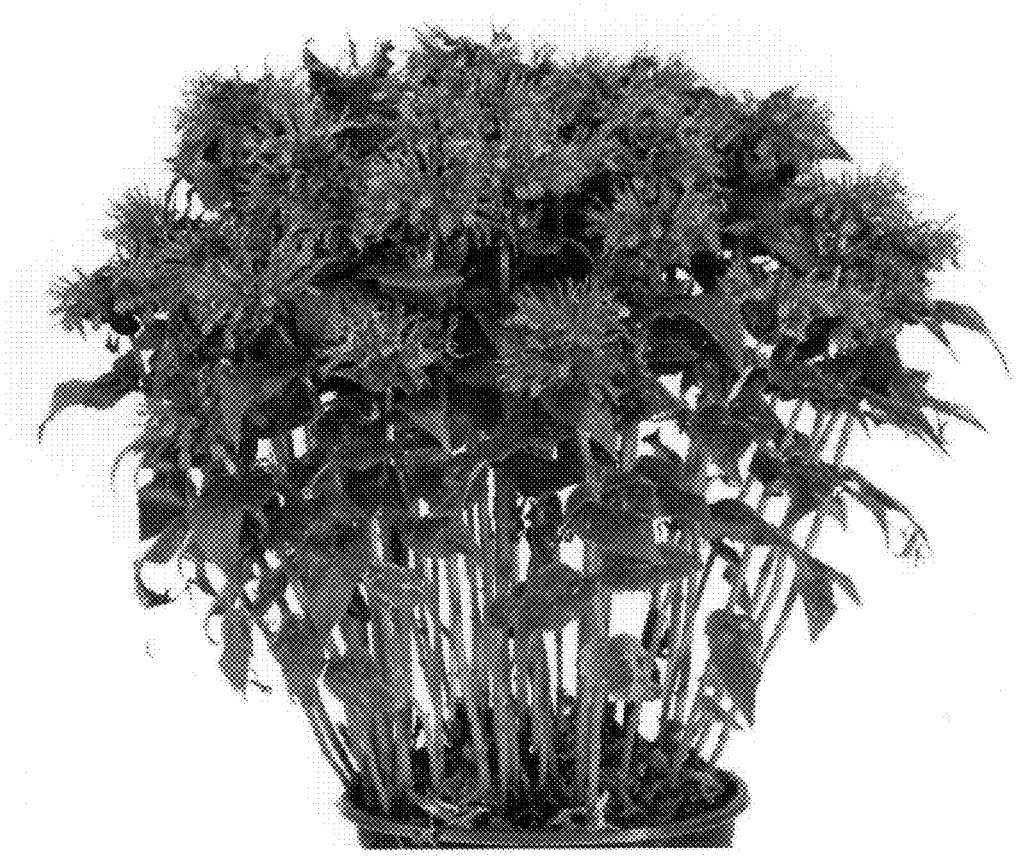
Figure 2:
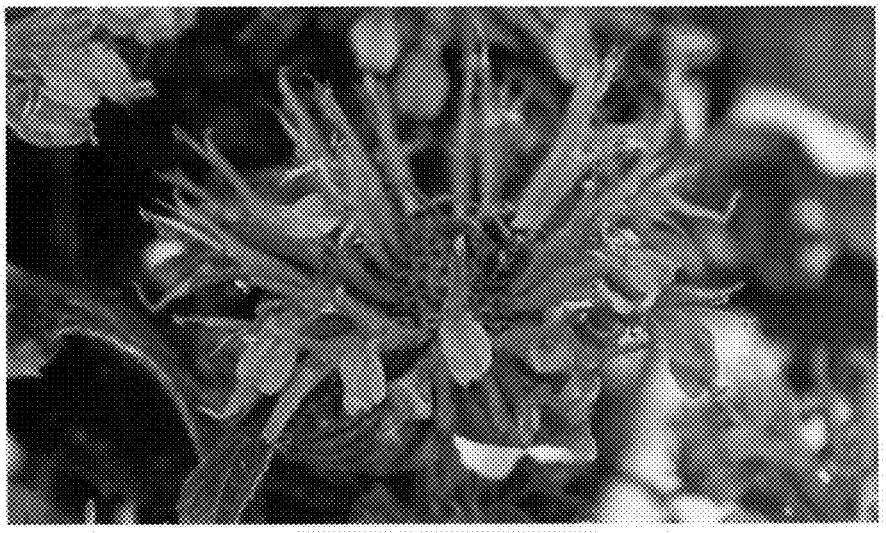

The Photograph in FIG. 2 provides a view of an inflorescence of 'Purple Lace'.

Figure 3:
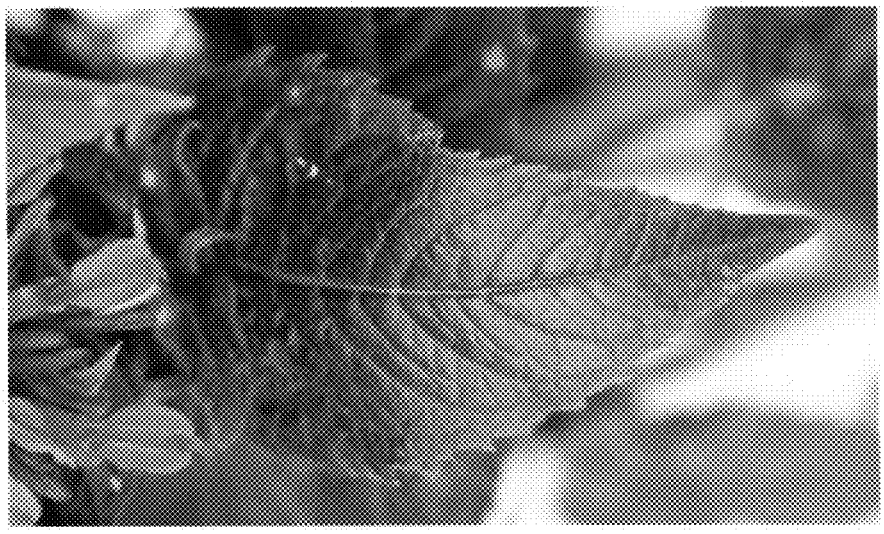

The Photograph in FIG. 3 provides a close-up view of a leaf of 'Purple Lace'.

The colors in the photographs are as close as possible with digital photography techniques available and the color values cited in the detailed botanical description accurately describe the colors of the *Monarda.*

DETAILED BOTANICAL DESCRIPTION

The following is a detailed description of two-year old plants of the new cultivar as grown outdoors in 17-cm containers in Rijpwetering, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—July through September in Rijpwetering, The Netherlands.

*Plant habit.*—Compact with strong upright stems.

*Height and spread.*—Reaches about 36 cm in height and 43 cm in spread.

*Hardiness.*—At least to U.S.D.A. Zone 5.

*Diseases.*—No susceptible or resistance has been observed.

*Propagation*—Stem cuttings and tissue culture.

*Growth rate.*—Moderate.

Stem description:

*Stem shape.*—Quadrangular.

*Stem color.*—144A.

*Stem aspect.*—Upright and strong.

*Stem surface.*—Very slightly glossy and sparsely covered with very short pubescent hairs; average of 0.5 mm in length and NN155C to NN155D in color.

*Branching.*—Main stems grow from the base and have no lateral branches, average of 48, average length is 31.6 cm and 0.45 cm in diameter.

Foliage description:

*Leaves.*—Opposite arrangement, ovate in shape, truncate to cordate base, acute apex, serrate margins, slightly glossy and rugose on upper surface and lower surface, both surfaces covered with short hairs, moderately on upper surface and more heavily on the lower surface especially on the main vein and secondary veins; hairs 0.75 mm in length and NN155C to NN155D in color, color young and mature upper surface N137A, color young and mature lower surface 137B, veins on upper surface are 152D, veins on lower surface are 145C.

*Petioles.*—Average of 0.35 cm in length and 2 mm in diameter, color of upper surface and lower surface 145C, sparsely pubescent surface.

Inflorescence description:

*Inflorescence type.*—Terminally verticillaster.

*Inflorescence number.*—1 per lateral stem.

*Inflorescence fragrance.*—Pleasant and spicy.

*Inflorescence size.*—Average of 3.7 cm in depth and 6.6 cm in diameter.

*Peduncles.*—None, sessile to stem.

*Bracts.*—An average of 26 bracts, average of 2 cm in length and 0.8 cm in width, narrow ovate to linear in shape, a blend of 143A and 144D in color, covered on both surfaces with pubescence that matches the bract color.

*Flower buds.*—Narrow oblanceolate in shape and curved, average of 2.3 cm in length and 2.5 mm in width, 72A in color with base 72B.

*Flower longevity.*—Approximately 5 days.

*Flower type.*—Labiate.

*Flower quantity.*—Average of 50 per verticillaster.

*Flower size.*—Average of 6 mm in diameter and 3.1 cm in depth.

*Sepals.*—5 per verticillaster, dull and tubular in appearance, rotate and tubular in arrangement, fused tubular tips are 15% free, margins of free part are entire, sepals are fused, base is fused into tubular shape, average of 7 mm in length and 0.5 mm in width (measured at the base of the free tip), color: immature and mature upper and lower surfaces are 195A, tinged with 174A, tip is 200A.

*Calyx.*—Tubular in shape, 7 mm in length and 2.5 mm in diameter.

*Petals.*—5, 2 fused petals forming upper lip; upper lip hooded, lanceolate in shape, lower 55% fused, about 2.9 cm in length and 2 mm in width, entire margin, emarginate apex, 3 fused petals forming lower lip; lower lip a single lobe, oblanceolate in shape, with a caudate apex, lower 55% fused, wavy margin, average of 2.9 cm in length and 6 mm in width, both lips; labiate in arrangement, both surfaces dull and moderately covered with very short glandular hairs an average of 0.3 mm in length and 72A to 72B in color, color when opening and fully open upper surfaces 72A to 72B, color when opening and fully open lower surface 72A and fading to 72C.

Reproductive organs:

*Pistils.*—1, stigma 2.7 mm in length, unequally cleft and 77A in color, style 2.6 cm in length and 77B in color, ovary is 145D in color and minute and covered by the base of the calyx.

*Stamens.*—2, filaments 1.3 cm in length and 72C in color, anthers are dorsifixed and narrow elliptic in shape, 2 mm in length and 72B in color, pollen is moderate and 158D in color.

*Seeds and fruit.*—None observed to date.

It is claimed:

1. A new and distinct cultivar of *Monarda* plant named 'Purple Lace' as herein illustrated and described.

* * * * *